US006376686B1

(12) United States Patent
Balan

(10) Patent No.: US 6,376,686 B1
(45) Date of Patent: Apr. 23, 2002

(54) DIRECT EPOXIDATION PROCESS

(75) Inventor: Prakash G. Balan, Wilmington, DE (US)

(73) Assignee: ARCO Chemical Technology, L.P., Greenville, DE (US)

( * ) Notice: Subject to any disclaimer, the term of this patent is extended or adjusted under 35 U.S.C. 154(b) by 0 days.

(21) Appl. No.: 09/946,321

(22) Filed: Sep. 5, 2001

(51) Int. Cl.⁷ ............................................. C07D 301/06
(52) U.S. Cl. ........................................ 549/532; 549/533
(58) Field of Search ................................. 549/532, 533

(56) References Cited

U.S. PATENT DOCUMENTS

| 4,207,275 A | 6/1980 | Stanton, Jr. et al. .......... 261/93 |
| 4,454,078 A | 6/1984 | Engelbrecht et al. ......... 261/93 |
| 4,468,130 A | 8/1984 | Weetman ..................... 366/330 |
| 4,833,260 A | 5/1989 | Neri et al. ................... 549/531 |
| 4,896,971 A | 1/1990 | Weetman et al. ............ 366/330 |
| 5,623,090 A | 4/1997 | Haruta et al. ................ 568/360 |
| 5,859,265 A | 1/1999 | Muller et al. ................ 549/531 |
| 5,972,661 A | 10/1999 | Kubera et al. .............. 435/104 |
| 6,005,123 A | 12/1999 | Dessau et al. .............. 549/531 |

FOREIGN PATENT DOCUMENTS

| JP | 4-352771 | 12/1992 |
| WO | WO 98/00413 | 1/1998 |

*Primary Examiner*—Ba K. Trinh
(74) *Attorney, Agent, or Firm*—Kevin M. Carroll

(57) ABSTRACT

The invention is an olefin epoxidation process that comprises reacting olefin, oxygen, and hydrogen in a liquid medium in the presence of an epoxidation catalyst in a reactor system comprising a tank, a tube, a plurality of impellers, and means for inhibiting flow. The reactor system facilitates transfer of the hydrogen and oxygen to the liquid medium.

15 Claims, No Drawings

US 6,376,686 B1

DIRECT EPOXIDATION PROCESS

FIELD OF THE INVENTION

This invention relates to an epoxidation process comprising reacting an olefin, hydrogen and oxygen in a liquid medium in the presence of a solid epoxidation catalyst in a reactor system that facilitates transfer of the hydrogen and oxygen to the liquid and the solid epoxidation catalyst.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethyl benzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Hydrogen peroxide is another oxidizing agent useful for the preparation of epoxides. Olefin epoxidation using hydrogen peroxide and a titanium silicate zeolite is demonstrated in U.S. Pat. No. 4,833,260. One disadvantage of both of these processes is the need to pre-form the oxidizing agent prior to reaction with olefin.

Another commercially practiced technology is the direct epoxidation of ethylene to ethylene oxide by reaction with oxygen over a silver catalyst. Unfortunately, the silver catalyst has not proved very useful in epoxidation of higher olefins. Therefore, much current research has focused on the direct epoxidation of higher olefins with oxygen and hydrogen in the presence of a different catalyst system. In this process, it is believed that oxygen and hydrogen react in situ to form an oxidizing agent. Thus, development of an efficient process (and catalyst) promises less expensive technology compared to the commercial technologies that employ pre-formed oxidizing agents.

Many different catalysts have been proposed for use in the direct epoxidation of higher olefins. For example, JP 4-352771 discloses the epoxidation of propylene oxide from the reaction of propylene, oxygen, and hydrogen using a catalyst containing a Group VIII metal such as palladium on a crystalline titanosilicate. U.S. Pat. No. 5,859,265 discloses a catalyst in which a platinum metal, selected from Ru, Rh, Pd, Os, Ir and Pt, is supported on a titanium or vanadium silicalite. Other examples include gold supported on titanium oxide, see for example U.S. Pat. No. 5,623,090, and gold supported on titanosilicates, see for example PCT Intl. Appl. WO 98/00413.

Because the direct epoxidation of olefins requires the mass transfer of gases into a liquid in order to achieve maximum rate and selectivity, reactor designs that would facilitate this mass transfer are needed. Thus, favorable reactor designs are necessary to allow increased rates and selectivity in the process. U.S. Pat. No. 5,972,661 describes a mixing system for the circulation and gas-liquid contacting of liquids in a tank that is especially useful for bio-reaction process such as fermentation. However, U.S. Pat. No. 5,972,661 does not describe the use of the reactor system with solid catalysts to facilitate gas-liquid-solid mass transfer.

In sum, new direct epoxidation processes are required to allow for efficient gas-liquid-solid contact to achieve maximum rate and selectivity to epoxide. In particular, increasing the selectivity to epoxide, the productivity of the catalyst, and extending the useful life of the catalyst would significantly enhance the commercial potential of direct epoxidation.

SUMMARY OF THE INVENTION

The invention is an olefin epoxidation process that comprises reacting olefin, oxygen, and hydrogen in a liquid medium in the presence of an epoxidation catalyst in a reactor system for circulating a liquid medium in a tank that facilitates transfer of the hydrogen and oxygen to the liquid medium. The reactor system provides a high degree of liquid circulation and micro-mixing of a multiphase liquid medium, enabling the desired simultaneous contacting and mass transfer between the liquid phase in the tank with a gas and a solid epoxidation catalyst.

DETAILED DESCRIPTION OF THE INVENTION

The process of the invention comprises reacting an olefin, hydrogen and oxygen in a liquid medium in the presence of an epoxidation catalyst in a reactor system that facilitates transfer of the hydrogen and oxygen to the liquid medium. The reactor system comprises a tank, a tube in the tank wherein the tube has an axis and opposite ends, a plurality of impellers rotating about the axis, and means for inhibiting agitation-induced liquid swirl around the axis within the tank. The reactor system creates flow of the liquid medium in opposite directions inside the tube and outside the tube.

The process of the invention employs a solid epoxidation catalyst capable of producing an epoxide in the reaction of an olefin, hydrogen, and oxygen. Any catalyst that is capable of producing epoxide from the reaction of olefin, hydrogen, and oxygen can be used. These epoxidation catalysts are well-known in the art. Suitable catalysts typically comprise a include a titanium or vanadium zeolite and a noble metal, such as Au, Ag, Pt, Pd, Ir, Ru, or Os, as disclosed in U.S. Pat. No. 6,005,123, which is herein incorporated by reference. Other suitable catalysts include gold supported on titanium oxide, as disclosed in U.S. Pat. No. 5,623,090, which is herein incorporated by reference; and gold supported on titanosilicates, see for example PCT Intl. Appl. WO 98/00413. Preferred catalysts comprise palladium and a titanium zeolite.

Titanium zeolites comprise the class of zeolitic substances wherein titanium atoms are substituted for a portion of the silicon atoms in the lattice framework of a molecular sieve. Such substances are well known in the art. Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM-48, ZSM-12, and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

The epoxidation process of the invention comprises contacting an olefin, oxygen, and hydrogen in a liquid medium in the presence of the epoxidation catalyst. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$–$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

Oxygen and hydrogen are also required for the process of the invention. Although any sources of oxygen and hydrogen are suitable, molecular oxygen and molecular hydrogen are preferred.

Epoxidation according to the invention is carried out at a temperature effective to achieve the desired olefin epoxidation, preferably at temperatures in the range of 0–250° C., more preferably, 20–100° C. The molar ratio of hydrogen to oxygen can usually be varied in the range of $H_2:O_2=1:10$ to $5:1$ and is especially favorable at 1:5 to 2:1. The molar ratio of oxygen to olefin is usually 1:1 to 1:20, and preferably 1:1.5 to 1:10. Relatively high oxygen to olefin molar ratios (e.g., 1:1 to 1:3) may be advantageous for certain olefins. A carrier gas may also be used in the epoxidation process in addition to olefin, hydrogen, and oxygen. As the carrier gas, any desired inert gas can be used. The molar ratio of olefin to carrier gas is then usually in the range of 100:1 to 1:10 and especially 20:1 to 1:10.

As the inert gas carrier, noble gases such as helium, neon, and argon are suitable in addition to nitrogen and carbon dioxide. Saturated hydrocarbons with 1–8, especially 1–6, and preferably with 1–4 carbon atoms, e.g., methane, ethane, propane, and n-butane, are also suitable. Nitrogen and saturated $C_1$–$C_4$ hydrocarbons are the preferred inert carrier gases. Mixtures of the listed inert carrier gases can also be used.

Specifically in the epoxidation of propylene according to the invention, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

The amount of catalyst used and the time required for the epoxidation may be determined on the basis of the gas hourly space velocity, i.e., the total volume of olefin, hydrogen, oxygen and carrier gas(es) per unit hour per unit of catalyst volume (abbreviated GHSV). A GHSV in the range of 10 to 10,000 $hr^{-1}$ is typically satisfactory.

The epoxidation according to the invention is carried out in a liquid medium. It is advantageous to work at a pressure of 1–100 bars and in the presence of one or more solvents. Suitable solvents include, but are not limited to, lower aliphatic alcohols such as methanol, ethanol, isopropanol, and tert-butanol, or mixtures thereof, and water. Fluorinated alcohols can be used. It is also possible to use mixtures of the cited alcohols with water.

The process is performed in a reactor system that facilitates transfer of the hydrogen and oxygen to the liquid medium by creating flow of the liquid medium in opposite directions inside the tube and outside the tube. A suitable reactor system is described in U.S. Pat. No. 5,972,661, the teachings of which are incorporated herein by reference.

The reactor system comprises a tank, a tube in the tank wherein the tube has an axis and opposite ends, a plurality of impellers disposed within the tube and rotatable about the axis, and means for inhibiting agitation-induced liquid swirl around the axis within the tank.

The tank is any suitable container that is capable of holding the liquid medium for reaction. The tank will typically be cylindrical in shape with tank walls arranged vertically upright. The tank contains a tube that is typically a cylindrical draft tube that is mounted within the tank. The tube is preferably mounted centrally within the tank, such that the axis of the tube and the axis of the tank are coincident. The tube is mounted such that there is clearance between the bottom of the tank and the lower end of the tube. The internal volume of the tube is preferably sufficient to hold between about 25 percent to about 50 percent of the volume of the liquid medium.

Within the tube, and rotatable about the tube's axis, are located a plurality of impellers. The impellers are typically attached to, and driven by, a shaft that is located on the tube's axis. One end of the shaft may be connected to a drive motor via a gear box and the opposite end of the shaft may be journaled in a steady bearing. The impellers are typically all of the same type, although different types of impellers may be used within the reactor system. Impellers are well-known in the art, and include axial flow impellers and radial flow impellers. Suitable axial flow impellers include pitched blade turbines (PBT), such as Model A200 available from the Lightnin Unit of General Signal Corporation, and airfoil-type blades (sometimes called hydrofoil blades), such as Lightnin Unit's A-315, which is described in U.S. Pat. No. 4,896,971, or other airfoil impellers which are described in U.S. Pat. No. 4,468,130. Suitable radial flow impellers include so-called Rushton turbines, such as Lightnin Unit's R-100 class of radial flow impellers. Other suitable radial flow impellers are described in U.S. Pat. Nos. 4,454,078 and 4,207,275. It is also possible to add additional impeller/impellers to the reactor system such that the additional impeller/impellers are located outside the draft tube, although still connected to the shaft that drives the plurality of impellers.

The impellers each produce a field or pattern of agitation that shears the liquid medium. The impellers are located in sufficiently closely spaced relationship along the axis and extend radially from the axis across the tube such that the agitation is established substantially throughout the entire volume of the tube. The plurality of impellers establish flow of the liquid medium in opposite directions in the tank between regions where reversal of the flow occurs. The flow of the liquid medium in one of the opposite directions is inside the tube and flow in the other of the opposite directions is outside the tube in the annular space between the tube wall and the tank wall.

The reactor system also comprises a means for inhibiting flow due to agitation which swirls around the axis. Such means may be provided by including in the tube a plurality of baffles. The plurality of baffles are typically sets of vertical baffles that are placed on the inner wall of the tube, such that they are located between the impellers. For instance, four vertical baffles will usually be are disposed symmetrically about the axis so that they are displaced 90° circumferentially about the axis of the shaft. In other words, two pairs of baffles are contained in each set and the pairs are 180° displaced with respect to each other. Other sets of baffles may be located above, and, if desired below, the upper and lower most impellers. The impellers, with the aid of the sets of baffles, produce a field or pattern of agitation which provide a high level of shear in the liquid in the draft tube. Thus, the pattern of agitation enhances mass transfer and promotes improved circulation in the tank.

The process may be performed using a continuous flow, semi-batch or batch mode of operation. The liquid medium, epoxidation catalyst, olefin, hydrogen and oxygen will typically be introduced into the reactor system at different injection points. However, one or more of the reactants may be introduced through the same injection point. In continuous or semi-batch operation, the reaction product will also be removed via an off-take line running from the reactor system.

I claim:

1. A process that comprises reacting an olefin, hydrogen and oxygen in a liquid medium in the presence of an epoxidation catalyst in a reactor system that facilitates transfer of the hydrogen and oxygen to the liquid medium, wherein the reactor system comprises:

(a) a tank;

(b) a tube in the tank, wherein the tube has an axis and opposite ends;

(c) a plurality of impellers disposed in the tube and rotatable about the axis such that the impellers each produce a field or pattern of agitation which shears the liquid medium, the impellers being in sufficiently closely spaced relationship along the axis and extending radially from the axis across the tube such that the agitation is established substantially throughout the entire volume of the tube, wherein the impellers establish flow of the liquid medium in one direction inside the tube and flow in the opposite direction outside the tube; and (d) means for inhibiting flow due to agitation which swirls around the axis.

2. The process of claim 1 wherein the olefin is a $C_2$–$C_6$ olefin.

3. The process of claim 1 wherein the olefin is propylene.

4. The process of claim 1 further comprising a carrier gas.

5. The process of claim 4 wherein the carrier gas is selected from the group consisting of helium, neon, argon, nitrogen, carbon dioxide, and $C^{1-8}$ saturated hydrocarbons.

6. The process of claim 4 wherein the carrier gas is propane.

7. The process of claim 1 wherein the liquid medium is a solvent selected from the group consisting of methanol, ethanol, isopropanol, and tert-butanol, and water.

8. The process of claim 1 wherein the liquid medium is water.

9. The process of claim 1 wherein the catalyst comprises palladium and titanium zeolite.

10. The process of claim 9 wherein the titanium zeolite is TS-1.

11. The process of claim 1 wherein the plurality of impellers are axial flow impellers.

12. The process of claim 1 wherein the plurality of impellers are radial flow impellers.

13. The process of claim 1 wherein the plurality of impellers are a combination of axial flow impellers and radial flow impellers.

14. The process of claim 1 wherein the means for inhibiting flow due to agitation which swirls around the axis comprises a plurality of baffles that are disposed between the impellers.

15. The process of claim 14 wherein the means for inhibiting flow due to agitation which swirls around the axis further comprises additional baffles that are located above the uppermost impeller and/or below the lowermost impeller.

* * * * *